US006706882B2

(12) United States Patent
Napoletano

(10) Patent No.: US 6,706,882 B2
(45) Date of Patent: Mar. 16, 2004

(54) PROCESS FOR THE PREPARATION OF (PYRIDINYLIDENE)-PHTHALIDES

(75) Inventor: Mauro Napoletano, Milan (IT)

(73) Assignee: Zambon Group S.p.A., Vicenza (IT)

( * ) Notice: Subject to any disclaimer, the term of this patent is extended or adjusted under 35 U.S.C. 154(b) by 0 days.

(21) Appl. No.: 09/958,972

(22) PCT Filed: Feb. 6, 2001

(86) PCT No.: PCT/EP01/01244

§ 371 (c)(1),
(2), (4) Date: Oct. 16, 2001

(87) PCT Pub. No.: WO01/60817

PCT Pub. Date: Aug. 23, 2001

(65) Prior Publication Data

US 2003/0023094 A1 Jan. 30, 2003

(30) Foreign Application Priority Data

Feb. 16, 2000 (IT) ..................................... MI2000A0261

(51) Int. Cl.⁷ ............................................. C07D 405/04
(52) U.S. Cl. .................................. 546/284.1; 546/284.7
(58) Field of Search .............................. 546/284.1, 284.7

(56) References Cited

U.S. PATENT DOCUMENTS 6,297,257 B1   10/2001   Napoletano et al.
6,329,370 B1   12/2001   Napoletano et al.
6,340,684 B1    1/2002   Napoletano et al.

OTHER PUBLICATIONS

R. H. Prager, et al., Tetrahedron, vol. 40, No. 9, pps. 1517–1522, "The Chemistry of Phthalide–3–Carboxylic Acid—1 Decarboxylation on the Presence of Aldehydes", 1984.
J. Ploquin, et al., J. Heterocycl. Chem., vol. 17, No. 5, pps. 961–973, "B–Diceto Enamines Heterocycliques: 1. Indanediones–1,3 Substituees EN 2 Par Un Heterocycle Azote", 1980.

*Primary Examiner*—Taofiq A. Solola
(74) *Attorney, Agent, or Firm*—Oblon, Spivak, McClelland, Maier & Neustadt, P.C.

(57) ABSTRACT

A process for the preparation of (pyridinylidene)-phthalides starting from 3-oxo-1,3-dihydro-isobenzofuran-1-carboxylic acids and pyridinecarbaldehydes, is described.

10 Claims, No Drawings

PROCESS FOR THE PREPARATION OF (PYRIDINYLIDENE)-PHTHALIDES

This APPLN is A 371 of PCT/EP01/01244 filed Jun. 28, 2001

FIELD OF THE INVENTION

The present invention relates to a process for the preparation of (pyridinylidene)-phthalides and, more particularly, relates to a process for preparing (pyridinylidene)-phthalides starting from 3-oxo-1,3-dihydro-isobenzofuran-1-carboxylic acids and pyridinecarbaldehydes. The (pyridinylidene)-phthalides are known compounds, described in the literature.

In the International patent applications WO 98/35958 in the name of Novartis and WO 00/05218 in the name of the same applicant various (pyridinylidene)-phthalides are used as useful intermediates for preparing phthalazines endowed with inhibitory activity of angiogenesis and PDE4 enzyme respectively.

BACKGROUND OF INVENTION

Several methods for synthesizing arylidenephthalides are known and some of them, particularly, have been employed for preparing (pyridinylidene)-phthalides.

For instance J. Ploquin et al. In *J. Het. Chem.* (1980), 17, 961 report the preparation of (pyridinylidene)-phthalides by hot condensation between phthalic anhydride and methylpyridines. This reaction, however, has a poor applicative interest because, besides presenting poor yields, it is limited to obtain unsubstituted or symmetrically substituted on the phthalic ring derivatives. In fact an asymmetrical substitution would inevitably lead to the formation of regioisomers difficult to separate.

A different process for preparing, inter alia, (pyridinylidene)-phthalides also asymmetrically substituted, reported in the already cited patent application WO 00/05218, is based on the Wittig condensation between a phosphonium salt XI and an aldehyde XII as here depicted:

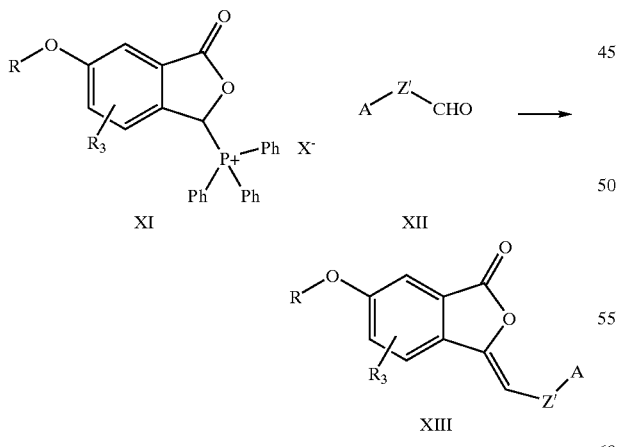

wherein A also represents pyridine and Z' can be absent.

Nevertheless this process, although it has a pratically quantitative yield, presents a series of disadvantages that make it of poor industrial interest.

In fact the preparation of the phosphonium salt XI, that occurs according to the following schema:

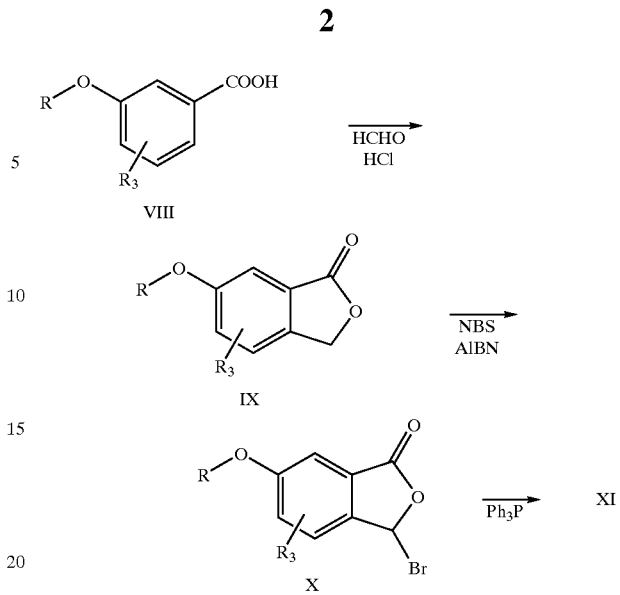

shows some critical points. Particularly the radicalic bromuration reaction of XI is strongly esothermic, the resultant bromurated product X is unstable and therefore it must be quickly used in the reaction with triphenylphosphine to give the phosphonium salt XI.

Lastly during this last step the molecular weight of the substrate increases considerably involving an undesired increase of the reaction mass. Besides, in the subsequent Wittig reaction the formation of equimolar quantities of phosphineoxide occurs that ulteriorly complicates the synthetic feasibility.

All these problems make the above mentioned process hardly practicable at industrial level. Among the known alternative methods for preparing arylidenephthalides it is of particular interest the one described by R. H. Pager et al. in *Tetrahedron*, (1984), 40, 1517 that uses differently substituted benzaldehydes (4) and 3-oxo-1,3-dihydro-1-isobenzofurancarboxylic acid (1) as starting products.

In all the examined cases the reaction, performed directly by heating the mixture of the reagents, leads to the formation of mixtures of 3-arylidene-phthalides (3) and 3-(arylhydroxymethyl)-phthalides (2) in variable ratios, with overall yields from 47 to 90%.

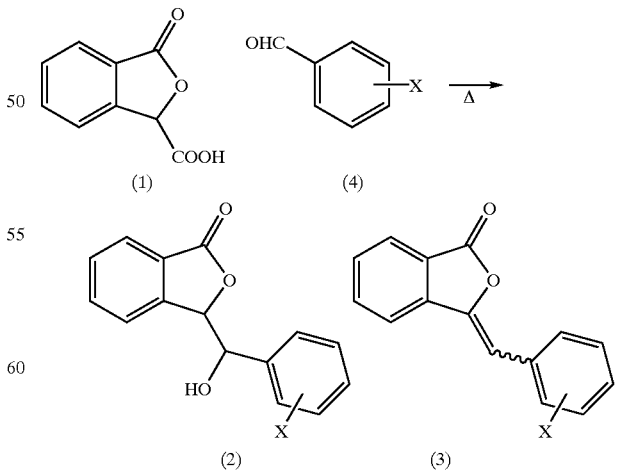

The authors study the course of the above reported decarboxylation-condensation reaction by varying some experimental parameters, such as the type and the quantity of aldehyde, the solvent absence or presence, the reaction time and temperature.

Regarding the influence exerted by the substituents of the aldehyde (4) upon the course of the reaction the authors declare that "only in the case of electrondonor groups merely the dehydration product (3) is obtained " (see lines 24, 1$^{st}$ column, page 1519).

Besides, it seems that the reaction is advantageous only if it is performed without a solvent while it results clearly disadvantageous if it is performed in its presence. In particular in apolar solvents a 140° C. it doesn't occur, while in the case of polar solvents, such as e.g. dimethylsulfoxide, it exclusively leads to obtain the alcohol (2) with poor fields and only with relevant excesses (2–6 equivalents) of aldehyde (see from line 19 forward, 1$^{st}$ column, pag. 1519). Moreover the dehydation of (2) to (3) doesn't occur appreciably in this solvent. Therefore from the work presented by Rolf H. Prager et al. it may be concluded that in order to obtain directly the compounds of formula (3) with significant yields the above mentioned reaction should be performed starting from electron-rich aldehydes (4) by heating in the absence of a solvent.

On the contrary we have surprisingly found that also using electron-poor aldehydes such as the pyridinecarbaldehydes, even in almost stechiometric ratio it is possible to obtain directly the corresponding arylidenephthalides with high yields if the reaction is performed in the presence of anhydrides.

With reference to this it has been hypothesized that the anhydride, besides probably acting as a dehydrator, is directly involved in the initial activation of the carboxylic function of the 3-oxo-1,3-dihydro-isobenzofuran-1-carboxylic acids.

BRIEF SUMMARY

Therefore object of the present invention is a process for preparing pyridinylidene-phthalides of formula

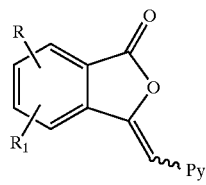

(I)

wherein

Py represents a 2, 3 or 4-pyridinyl group optionally substituted by one or more substituents selected from halogen, nitro, cyano, oxo and carboxy groups;

R and R$_1$, which may be the same or different, represent hydrogen, C$_1$–C$_6$ alkyl or a group OR$_2$ wherein R$_2$ represents a linear or branched C$_1$–C$_6$ alkyl, a C$_4$–C$_7$ cycloalkyl or a C$_1$–C$_6$ polyfluoroalkyl;

The bond ⁄⁄⁄ indicates both the isomers E and Z;

by reaction of a compound of formula

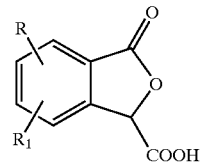

(II)

wherein R and R$_1$ have the above reported meanings; with an aldehyde of formula Py-CHO (III)

wherein Py has the above reported meaning;
by heating the mixture of the compounds having formula II and III in the presence of an anhydride and optionally in admixture with a suitable solvent.

DETAILED DESCRIPTION OF THE INVENTION

The process object of the present invention can be easily performed and it allows to obtain pyridinylidene-phthalides of formula I with good yields without using the aforesaid phosphonium salt XI.

The process object of the present invention provides for the reaction between a compound of formula II and a compound of formula III.

The compounds of formula II are known and easily obtainable for instance according to the synthetic route described in J. Chem. Soc. (1929), 200.

In the compounds of formula II the groups R and R$_1$ have the above reported meanings.

Particularly preferred compounds of formula II are those wherein at least one between R and R$_1$ represents OR$_2$, even more preferred those wherein one or both between R and R$_1$ are OCH$_3$.

Also the starting compounds of formula III are generally known, commercially available or obtainable according to processes reported in the literature.

Particularly preferred compounds of formula III are those wherein Py represents a 4-pyridinyl group, even more preferred if Py represents a dihalosubstituted 4-pyridinyl residue. In the process object of the present invention the compounds of formula III are generally used with respect to the compounds of formula II in a molar ratio from 0.5 to 4. Preferably they are used in a ratio from 0.8 to 1.5, even more preferably from 0.9 to 1.1.

The present process is performed in the presence of an anhydride.

The term "anhydride" means a reagent selected in the group of the organic or inorganic anhydrides, respectively derived from organic or inorganic acids, or mixed, including in this class also the acyl, alkyl and arylsulfonyl halides.

Examples of anhydrides utilizable in the present process are, in the case of the organic anhydrides, acetic, trifluoroacetic, or trifluoromethansulfonic anhydride, in the case of inorganic anhydrides, phosphoric or sulphuric anhydride or thionylchloride, while among the mixed anhydrides, acetyl, tosyl or mesyl chloride, these acyl chlorides being consider herewith as anhydrides of an organic acid and hydrogen chloride.

This, for example, acetyl chloride is the mixed anhydride of acetic acid and hydrogen chloride.

The organic anhydrides are particularly preferred.

For practical reasons acetic anhydride is preferably used.

In the process object of the present invention the above cited anhydride can be employed in a large excess as regards the starting compound of formula n acting also as solvent, for example in a molar ratio of 10:1 as regards the compound of formula II.

Alternatively the anhydride can be used as regards the compound III in a narrower molar ratio, for example from 1 to 3. In that case the reaction may request the presence of an appropriate co-solvent.

In this connection examples of usable solvents are high boiling apolar solvents such as for example the aromatic hydrocarbons, optionally chlorosubstituted.

Preferred aromatic solvents are toluene, xylene and chlorobenzene, particularly preferred is toluene.

For practical reasons the process object of the present invention is preferably performed in an excess of acetic anhydride.

Also the usage of other activating systems, such as for example the Lewis acids, or dehydrators, such as the distillation of appropriate azeotropic mixtures, falls, moreover, within the scope of the present invention as an alternative to the anhydride.

The present process is performed by heating the mixture of the compounds of formula II and III, in the presence of the anhydride and optionally of the appropriate solvent.

Preferably the reaction mixture is heated at the reflux temperature.

The process object of the present invention allows to obtain a final raw product essentially constituted by the mixture E/Z of the compounds of fomula I, usable directly without further treatment of purification.

The compounds of formula I, prepared according to the process object of the present invention, can for example be directly used in the synthesis of PDE4 inhibitors having a phthalazinic structure, as described in the already cited International application WO 00/05218.

Said compounds have the formula

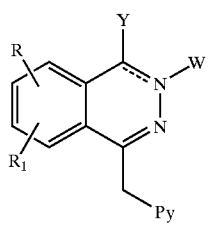

(IV)

wherein

R, R$_1$ and Py have the above reported meanings;

--------- is a single or double bond;

Y represents two hydrogen atoms or a group =O when --------- is a single bond, or when --------- is a double bond Y is hydrogen cyano, (C$_1$–C$_4$)-alkoxycarbonyl, amido, optionally sustituted aryl or heterocyclyl, (C$_1$–C$_8$)-alkyl, (C$_1$–C$_8$)-cyclylamino;

W is absent when --------- is a double bond or, when --------- is a single bond, it represents a) hydrogen;

b) (C$_1$–C$_6$)-alkyl optionally substituted by aryl, heterocyclyl or by a group COR$_5$ wherein R$_5$ is hydroxy, (C$_1$–C$_4$)-alkoxy or hydroxyamino:

c) —COR$_6$ wherein R$_6$ is hydrogen, aryl, aryl-(C$_1$–C$_6$)-alkyl, optionally alkylated or monohydroxylated amino, hydroxy, (C$_1$–C$_4$)-alkoxy, carboxy, (C$_1$–C$_4$)-alkoxycarbonyl,

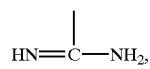

or (C$_1$–C$_4$)-alkyl optionally substituted by a heterocycle;

d) (C$_1$–C$_4$)-alkylsulfonyl.

The present process is preferably applied to the synthesis of 4-pyridinyl derivatives, even more preferably to the synthesis of dihalo-substituted 4-pyridinyl derivatives. The application of the present process to the synthesis of 3-[(3,5-dichloro-4-pyridinyl)methylene]-6-methoxy-1-(3H)-isobenzofuranone is particularly preferred.

In a preferred embodiment of the process object of the present invention, the mixture of the compound II, the compound III and the anhydride is refluxed until the reaction is complete. The mixture is evaporated and the residue, recovered with the appropriate solvent and rievaporated up to dryness, can be directly used in the following step.

The process object of the present invention is advantageous chiefly for the simplicity of realization and therefore it is particularly suitable for the industrial application.

It allows to prepare the compounds of formula I with high yields and in a short time without using the above mentioned phosphonium salt XI, avoiding therefore the relative problems, such as for example the formation of unstable bromurated intermediates through exothermic reactions, the considerable increase of molecular weight and the formation of phosphineoxides.

A further reason of interest is the obtainment of a raw product usable directly in the subsequent reaction without requesting further purifications.

Besides, as regards the already cited synthetic process reported in the International application WO 00/05218, the present process allows to reduce the total number of steps starting from the same benzoic acid derivative precursor.

With the aim to better illustrate the present invention the following examples are now given.

EXAMPLE 1

Preparation of 3-[(3,5dichloro4-pyridinyl)methylene]-6-methoxy-1-(3H)-isobenzo-furanone The mixture prepared at room temperature of 5-methoxy-3-oxo-1,3-dihydro-1-isobenzofurancarboxylic acid (12.4 g; 0.06 moles), prepared as described in *J Chem. Soc.* (1929), 200, and 3,5-dichloro-4-pyridinecarbaldehyde (10.8 g; 0.061 moles), prepared according to *Heterocycles* (1995), 41, 675, in acetic anhydride (60 ml) was refluxed, under stirring, for 30 minutes.

The reaction was evaporated under vacuum, collected with toluene (50 ml) and evaporated again. This treatment was repeated for other two times obtaining the desired compound (19.3 g; quantitative yield) as a yellow solid.

$^1$H—NMR (200 MHz, CDCl$_3$) δ (ppm): 8.60 and 8.50 (s, 2H, Py); 7.77–6.20 (m, 4H, Ar and CH); 3.90 and 3.80 (s, 3H, OMe); isomeric ratio 9:1.

EXAMPLE 2

Preparation of 4-[(3,-dichloro-4-pyridinyl)methyl]-1,2-dihydro-7-methoxy-1-phthalazinone In a 4 liter reactor at room temperature 3-[(3,5-dichloro-4-pyridinyl)methylene]-6-methoxy-1-(3H)-isobenzofuranone (335 g; 1.04 moles), prepared as described in the example 1, and methanol (1785 ml) were charged. Then acetic acid (178 ml) and, maintaining the temperature under 40° C. by external cooling, hydrazine monohydrate (171.7 ml) were added by dripping.

The reaction mixture became a solution, then a new precipitate began to form. The mixture was refluxed for 2 hours. The end of the reaction was checked by TLC (a sample was drawn and diluted with $CH_2Cl_2$, elutant hexane:ethylacetate=7:3). When the reaction ended, the mixture was cooled at 0° C. and filtered. The filtrate was washed with methanol (215 ml). The solid was dried under vacuum at 40° C. obtaining the desired compound (328.5 g; yield 99%) as a light yellow solid.

EXAMPLE 3
Preparation of 3-[(3,5-dichloro-4-pyridinyl)methylen]-6-methoxy-1-(3H)-isobenzofuranone A mixture of 5-methoxy-3-oxo-1,3-dihydro-1-isobenzofurancarboxylic acid (5 g; 24 mmoles) and 3,5dichloro-4-pyridinecarboxaldehyde (4.3 g; 24 mmoles) in toluene (32.5 ml) and acetic anhydride (7.5 ml) was refluxed, under stirring, for 8 hours.

The mixture was cooled at 0° C. and filtered. The filtrate was washed with hexane.

The desired compound was obtained (5.6 g) as yellow solid.

Yield 73%

$^1$H—NMR in conformity with that reported in Example 1.

The same reaction was performed with 4.5 ml, 5 ml and 10 ml of acetic anhydirde. In all cases the yields were comparable. The reaction time was inversely proportioned to the acetic anhydride concentration.

EXAMPLE 4
Preparation of 3-[(3-chloro-4-pyridinyl)methylen]-6-methoxy-1-(3H)-isobenzofuranone A mixture of 5-methoxy-3-oxo-1,3-dihydro-1-isobenzofurancarboxylic acid (0.7 g; 3.4 mmoles) and 3-chloro-4-pyridinecarboxaldehyde (0.52 g; 3.7 mmoles), prepared as described in J. Organometallic Chem. (1981), 216, 139, in toluene (5 ml) and acetic anhydride (1 ml) was refluxed, under stirring, for 10 hours.

The mixture was cooled at 0° C. and filtered. The filtrate was washed with hexane.

The compound 3-[(3-chloro-4-pyridinyl)methylen]-6-methoxy-1-(3H)-isobenzofuranone was obtained (680 mg) as yellow solid.

Yield 70%

$^1$H—NMR (200 MHz, $CDCl_3$) δ (ppm): 8.58 (s 1H ClC=CH—N); 8.47 (d, 1H, JHH=5.3 Hz, N—*CH=CH), 8.11 (d, 1H, N—CH=*CH); 7.74 (d, 1H, JHH=8.5 Hz, *CH=CH—OMe); 7.35–7.28 (m, 2H, Ar); 6.61 (s, 1H, *CH-Py); 3.90 (s, 3H, $CH_3$—O).

EXAMPLE 5
Preparation of 3-[(3,5dichloro-4-pyridinyl)methylen]-6-methoxy-1(3H)-isobenzofuranone By following the same procedure as in Example 4 but by using trifluoroacetic anhydride instead of acetic anhydride, starting from 5-methoxy-3-oxo-1,3-dihydro-1-isobenzofurancarboxylic acid (100 mg) the desidered compound (109 mg) was obtained.

Yield 70%

$^1$H—NMR in conformity with that reported in Example 1.

What is claimed is:

1. A process for the preparation of pyridinylidenephthalides of formula

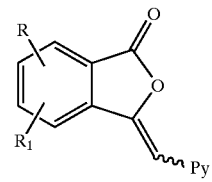

(I)

wherein
Py represents a 2, 3 or 4-pyridinyl group optionally substituted by one or more substituents selected from halogen nitro, cyano, oxo and carboxy;
R and $R_1$, which can be the same or different between them, represent hydrogen, $C_1$–$C_6$ alkyl or a group $OR_2$ wherein $R_2$ represents a linear or branched $C_1$–$C_6$ alkyl, a $C_4$–$C_7$ cycloalkyl or a $C_1$–$C_6$ polyfluoroalkyl;

The bond  indicates both the isomers E and Z:
which comprises the reaction of a compound of formula

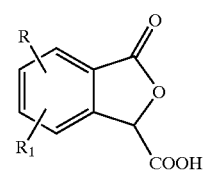

(II)

wherein R and $R_1$ have the meanings above reported; with an aldehyde of formula Py-CHO  (III)

wherein Py has the above reported meaning;
by heating of the mixture of the compounds of formula II and III in the presence of an anhydride and optionally in admixture with a suitable solvent.

2. The process according to claim 1 wherein Py represents a dihalosubstituted 4-pyridinyl group.

3. The process according to claim 2 wherein Py represents a 3,5-dichloro-4-pyridinyl group.

4. The process according to claim 1 wherein one or both between R and $R_1$ represent $OCH_3$.

5. The process according to claim 1 wherein the compounds of formula III are employed with respect to the compounds of formula II in a molar ratio from 0.5 to 4.

6. The process according to claim 5 wherein the compounds of formula III are employed with respect to the compounds of formula II in a molar ratio from 0.8 to 1.5.

7. The process according to claim 6 wherein the compounds of formula III are employed with respect to the compounds of formula II in a molar ratio from 0.9 to 1.1.

8. The process according to claim 1 wherein the anhydride is an organic anhydride.

9. The process according to claim 8 wherein the anhydride is acetic anhydride.

10. The process according to claim 1 wherein the anhydride is used in excess.

* * * * *